(12) United States Patent
Kriesel et al.

(10) Patent No.: US 8,029,468 B2
(45) Date of Patent: Oct. 4, 2011

(54) FLUID DELIVERY AND MIXING APPARATUS WITH FLOW RATE CONTROL

(75) Inventors: Marshall S. Kriesel, Saint Paul, MN (US); Joshua W. Kriesel, San Francisco, CA (US); Alan D. Langerud, Saint Paul, MN (US)

(73) Assignee: BioQuiddity, Inc., San Francisco, CA (US)

( * ) Notice: Subject to any disclaimer, the term of this patent is extended or adjusted under 35 U.S.C. 154(b) by 1597 days.

(21) Appl. No.: 11/353,593

(22) Filed: Feb. 13, 2006

(65) Prior Publication Data
US 2006/0206052 A1 Sep. 14, 2006

Related U.S. Application Data

(60) Provisional application No. 60/654,268, filed on Feb. 15, 2005.

(51) Int. Cl.
*A61M 37/00* (2006.01)
(52) U.S. Cl. ......... 604/131; 604/134; 604/135; 604/246
(58) Field of Classification Search ............... 604/82–92, 604/890.1, 131–135, 151, 246–247
See application file for complete search history.

(56) References Cited

U.S. PATENT DOCUMENTS

| 3,884,228 A | 5/1975 | Hahn |
| 5,380,287 A | 1/1995 | Kikuchi et al. |

*Primary Examiner* — Theodore Stigell
(74) *Attorney, Agent, or Firm* — James E. Brunton

(57) ABSTRACT

A dual reservoir fluid dispensing apparatus for use in controllably dispensing fluid medicaments, such as antibiotics, analgesics and like medicinal agents from either or both of the device reservoirs. The fluid dispensing apparatus includes novel fill means for selectively filling each of the reservoirs with the same or different medicaments that are to be dispensed to the patient. Stored energy sources are provided in the form of a pair of constant force spring members of novel design that provide the force necessary to continuously and substantially uniformly expel fluid from the reservoirs. The apparatus also includes novel adjustable flow rate assemblies that are disposed intermediate the outlet port of the fluid reservoirs and the outlet port of the device for precisely controlling the rate of fluid flow from the outlet port toward the patient.

20 Claims, 13 Drawing Sheets

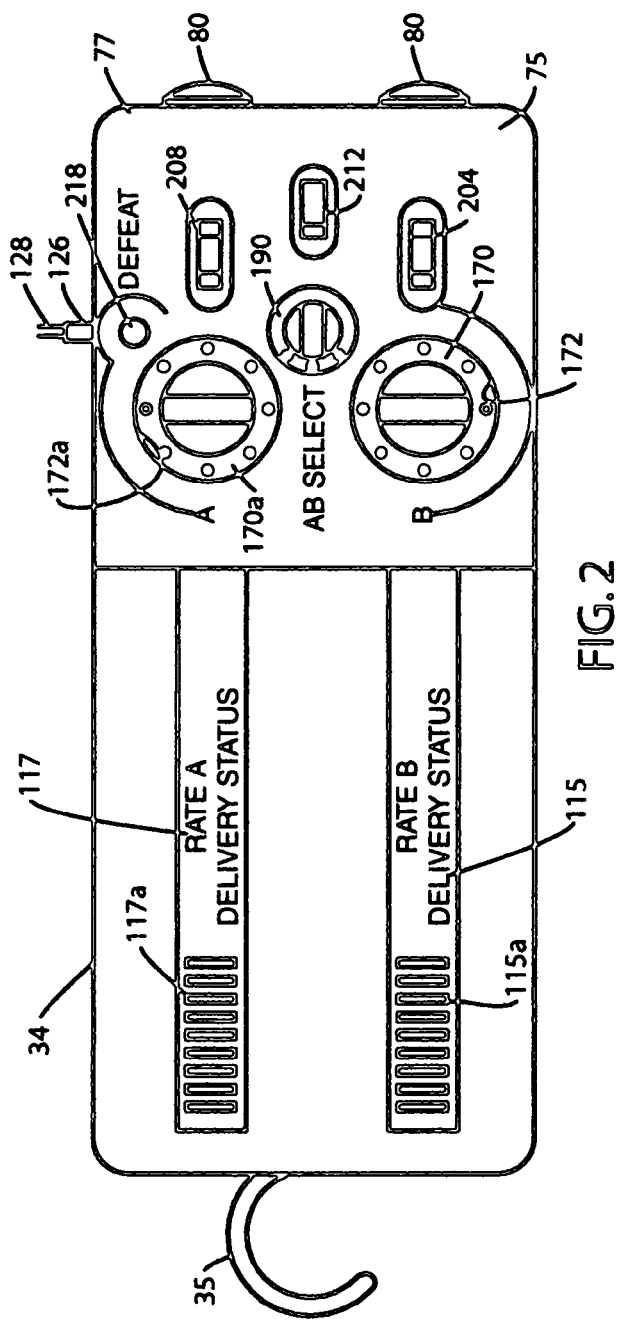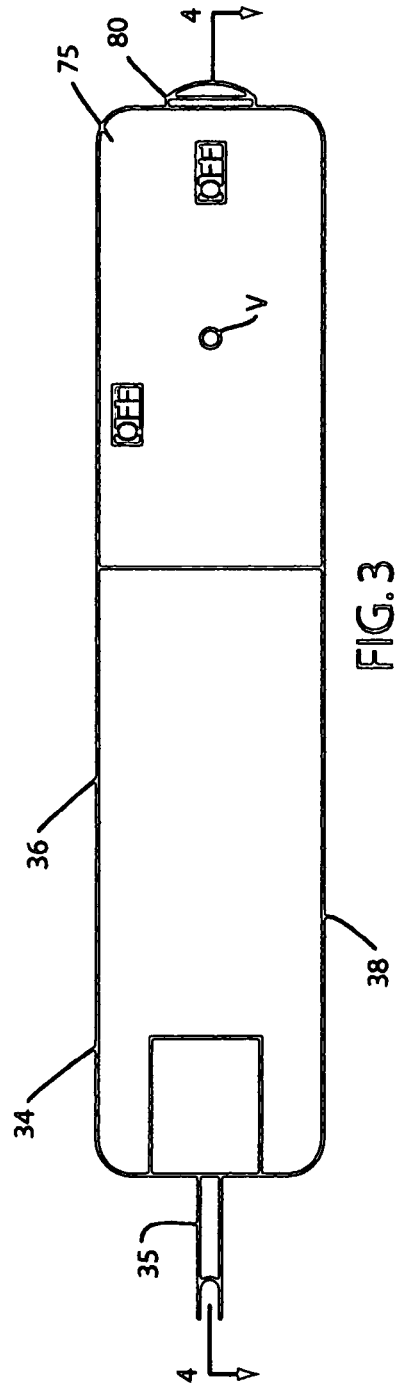

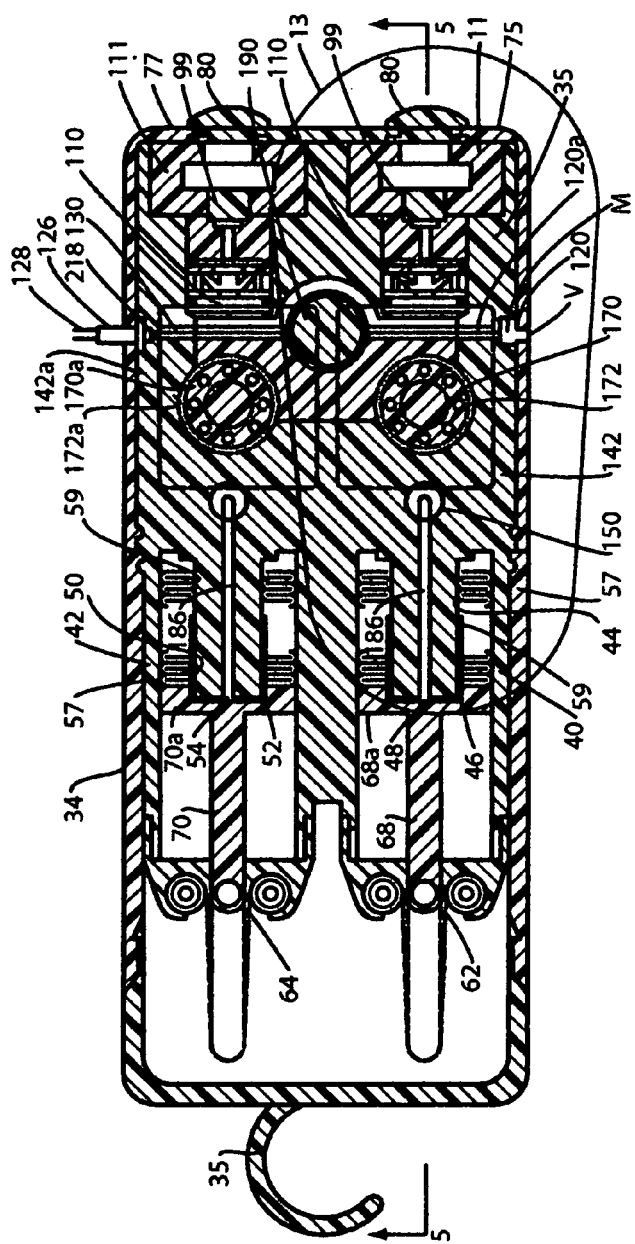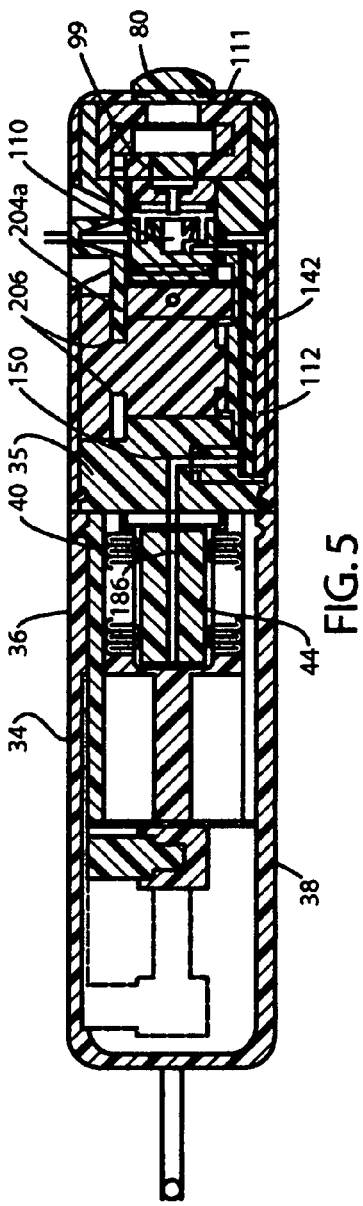
FIG. 4
FIG. 5

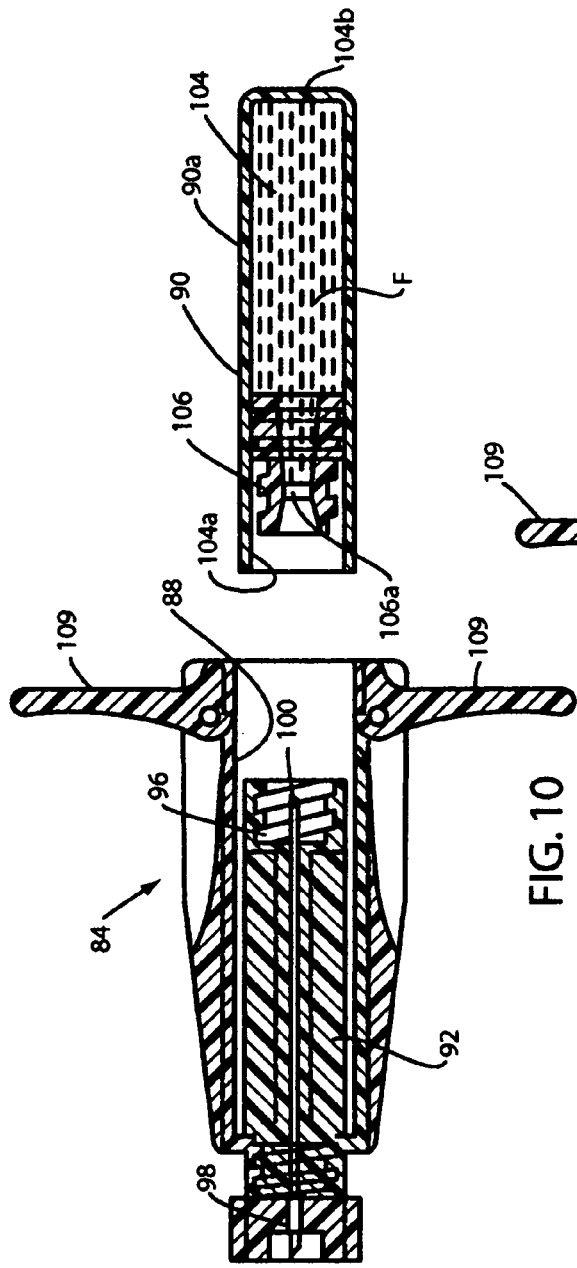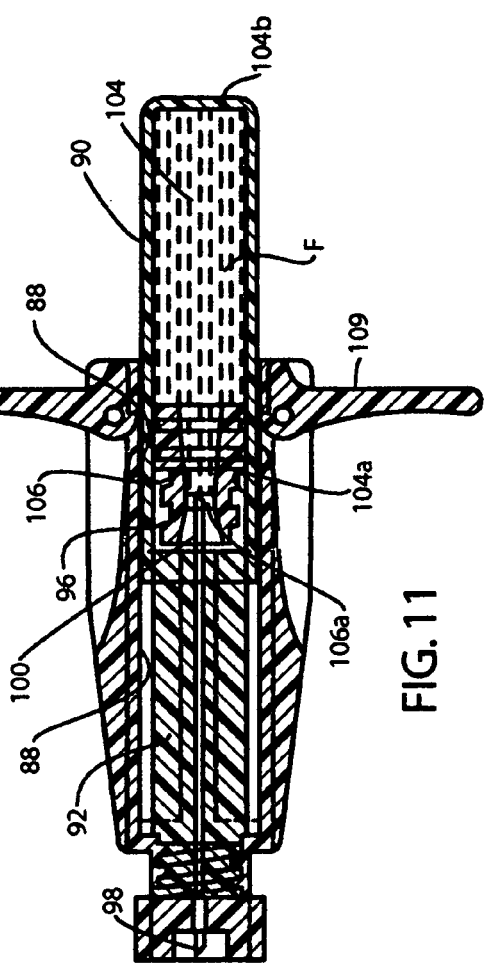
FIG. 10
FIG. 11

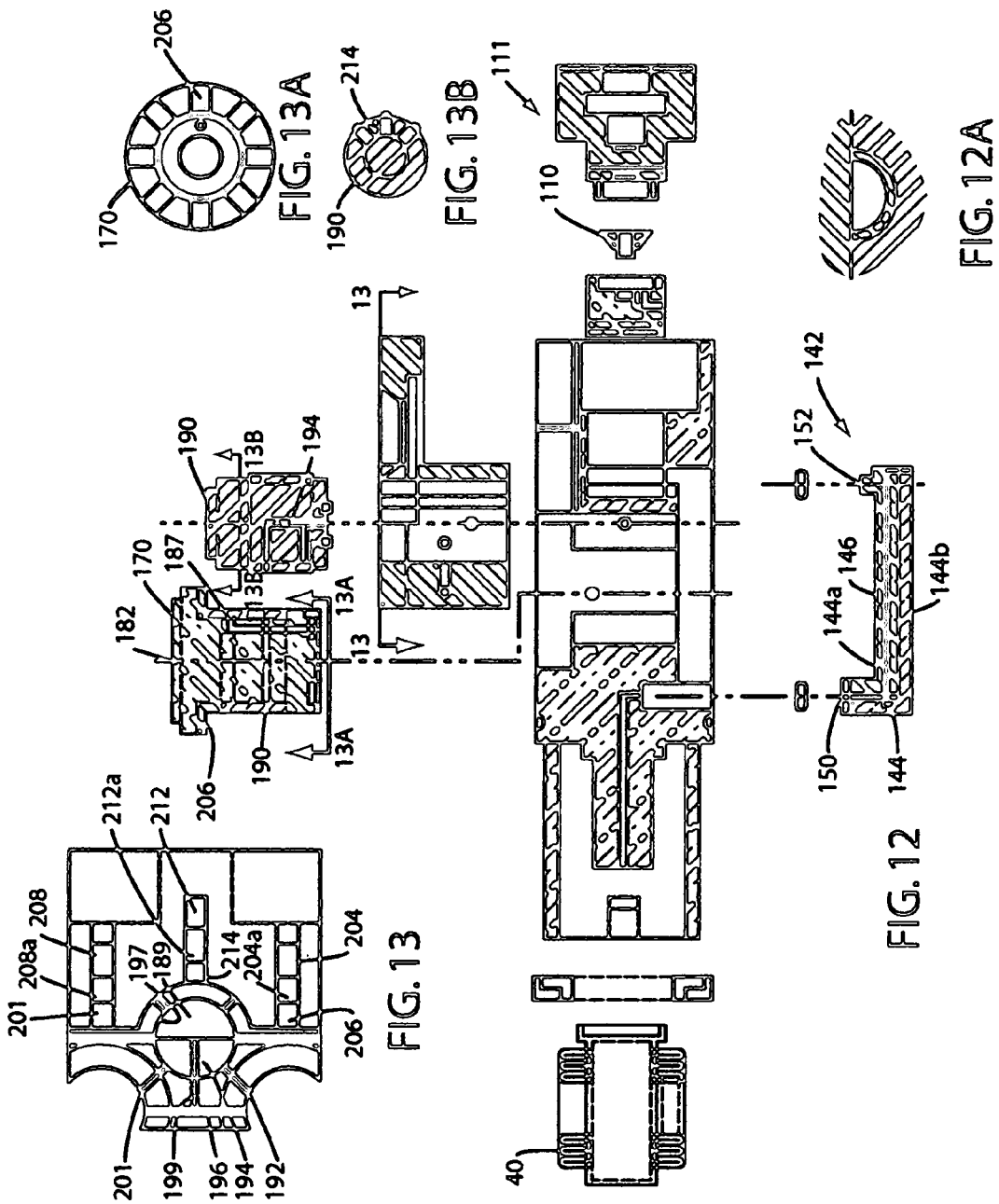

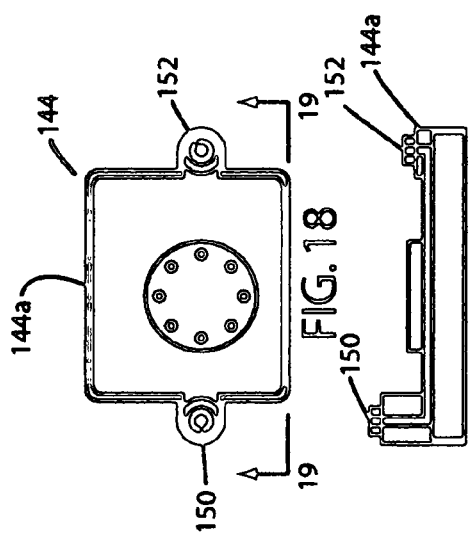
FIG. 18
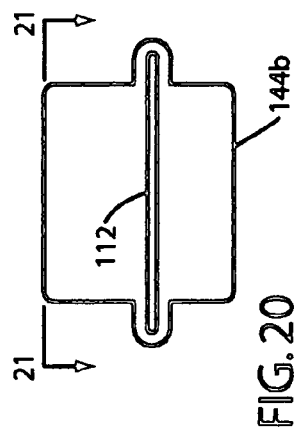
FIG. 19
FIG. 21
FIG. 20
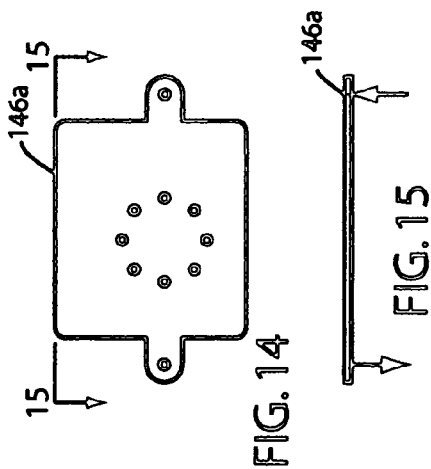
FIG. 14
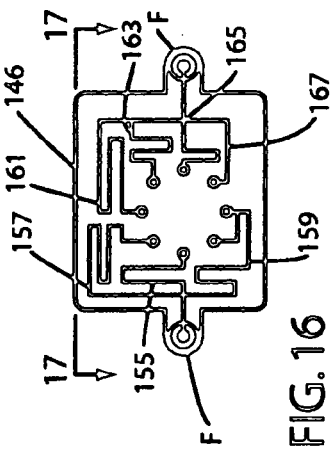
FIG. 16
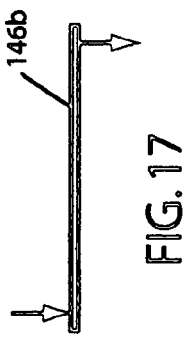
FIG. 15
FIG. 17

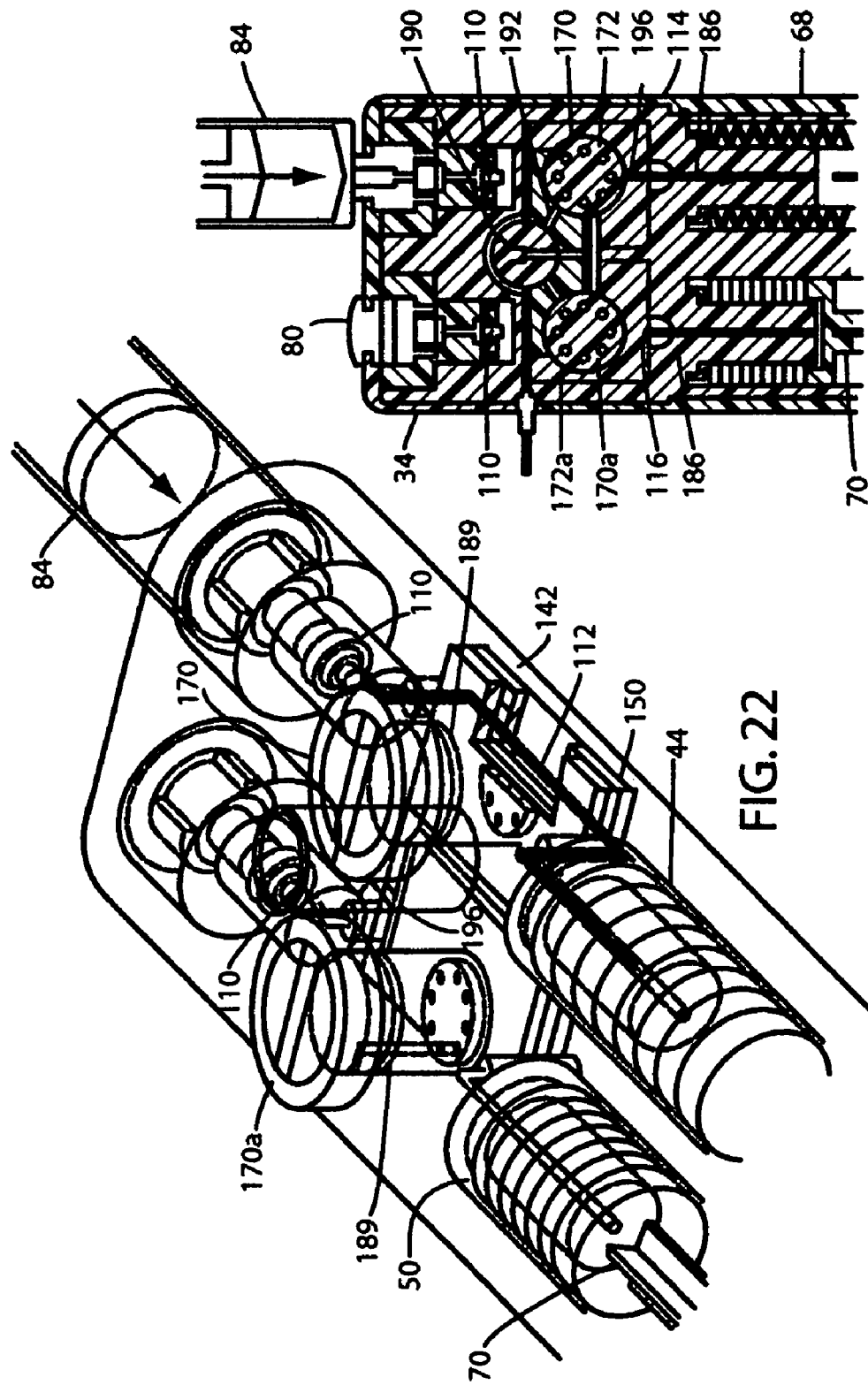

| Channel Type | Flow Rate at 0.5 ATM | Total Channel Length | Cross-sectional Dimensions Width X Depth | Channel Volume | Priming Time at a Pressure of Approximately 0.5 ATM |
|---|---|---|---|---|---|
| Priming channels on the chip | | 8 cm | 1000 μm x 100 μm | .080 ml | |
| Channel in the flow rate selector | | 3 cm | 1000 μm diameter* | .024 ml | |
| Administration line | | 100 cm | 1000 μm diameter* | .785 ml | |
| Priming channel + selector channel + administration line | 0.20 ml/sec | | 40 μm x 100 μm | .89 ml | 4.4 sec |
| 0.1 ml/hr channel | 0.1 ml/hr | 73 cm | 40 μm x 100 μm | $2.9 \times 10^{-3}$ ml | 104.0 sec[1] |
| 0.2 ml/hr channel | 0.2 ml/hr | 36.5 cm | 40 μm x 100 μm | $1.45 \times 10^{-3}$ ml | 25.1 sec |
| 0.3 ml/hr channel | 0.3 ml/hr | 24.3 cm | 40 μm x 100 μm | $9.67 \times 10^{-4}$ ml | 11.6 sec |
| 0.4 ml/hr channel | 0.4 ml/hr | 18.3 cm | 40 μm x 100 μm | $7.32 \times 10^{-4}$ ml | 6.5 sec |
| 0.5 ml/hr channel | 0.5 ml/hr | 14.6 cm | 40 μm x 100 μm | $5.84 \times 10^{-4}$ ml | 4.2 sec[2] |
| 0.6 ml/hr channel | 0.6 ml/hr | 12.2 cm | 40 μm x 100 μm | $4.88 \times 10^{-4}$ ml | 2.9 sec |
| 0.7 ml/hr channel | 0.7 ml/hr | 10.4 cm | 40 μm x 100 μm | $4.16 \times 10^{-4}$ ml | 2.1 sec |
| 0.8 ml/hr channel | 0.8 ml/hr | 9.1 cm | 40 μm x 100 μm | $3.64 \times 10^{-4}$ ml | 1.6 sec |
| 0.9 ml/hr channel | 0.9 ml/hr | 8.1 cm | 40 μm x 100 μm | $3.24 \times 10^{-3}$ ml | 1.3 sec |
| 1.0 ml/hr channel | 1.0 ml/hr | 62.5 cm | 100 μm x 100 μm | $6.25 \times 10^{-3}$ ml | 22.5 sec |
| 2.0 ml/hr channel | 2.0 ml/hr | 31.3 cm | 100 μm x 100 μm | $3.13 \times 10^{-3}$ ml | 5.6 sec |
| 3.0 ml/hr channel | 3.0 ml/hr | 20.8 cm | 100 μm x 100 μm | $2.08 \times 10^{-3}$ ml | 2.5 sec |
| 4.0 ml/hr channel | 4.0 ml/hr | 15.6 cm | 100 μm x 100 μm | $1.56 \times 10^{-3}$ ml | 1.4 sec |
| 5.0 ml/hr channel | 5.0 ml/hr | 12.2 cm | 100 μm x 100 μm | $1.25 \times 10^{-3}$ ml | .9 sec |
| 6.0 ml/hr channel | 6.0 ml/hr | 33.8 cm | 200 μm x 100 μm | $6.76 \times 10^{-3}$ ml | 2.4 sec |
| 10.0 ml/hr channel | 10.0 ml/hr | 35.2 cm | 300 μm x 100 μm | $1.06 \times 10^{-3}$ ml | 3.8 sec |
| 20.0 ml/hr channel | 20.0 ml/hr | 17.6 cm | 300 μm x 100 μm | $5.03 \times 10^{-3}$ ml | 1.0 sec |
| 30.0 ml/hr channel | 30.0 ml/hr | 11.7 cm | 300 μm x 100 μm | $3.53 \times 10^{-3}$ ml | .4 sec |
| 50.0 ml/hr channel | 50.0 ml/hr | 9.9 cm | 400 μm x 100 μm | $3.96 \times 10^{-3}$ ml | 2.9 sec |

FIG. 27

FLUID DELIVERY AND MIXING APPARATUS WITH FLOW RATE CONTROL

This is a Non-Provisional Application claiming the benefit of Provisional Application No. 60/654,268 filed Feb. 15, 2005.

BACKGROUND OF THE INVENTION

1. Field of the Invention

The present invention relates generally to fluid delivery devices. More particularly, the invention concerns an improved, dual reservoir apparatus for controllably mixing various medicinal agents and then delivering the agents into an ambulatory patient at specific rates over extended periods of time. One embodiment of the invention includes a novel adjustable flow rate control means for precisely controlling the rate of fluid flow from the reservoir of the device toward the patient.

2. Discussion of the Prior Art

Many medicinal agents require an intravenous route for administration of the medicament. The delivery device for delivering the medicament, while not an active pharmacologic agent, may enhance the activity of the drug by mediating its therapeutic effectiveness. Certain classes of new pharmacologic agents possess a very narrow range of therapeutic effectiveness, for instance, too small of a dose results in no effect, while too great of a dose results in a toxic reaction.

In the past, prolonged infusion of fluids has generally been accomplished using gravity flow methods, which typically involve the use of intravenous administration sets and the familiar bottle suspended above the patient. Such methods are cumbersome, imprecise and require bed confinement of the patient. Periodic monitoring of the apparatus by the nurse or doctor is required to detect malfunctions of the infusion apparatus. Devices from which liquid is expelled from a relatively thick-walled bladder by internal stresses within the distended bladder are well known in the prior art. Such bladder, or "balloon"-type, devices are described in U.S. Pat. No. 3,469,578, issued to Bierman and in U.S. Pat. No. 4,318,400, issued to Perry.

One of the most versatile and unique fluid delivery apparatus developed within recent years is that by one of the present inventors described in U.S. Pat. No. 5,205,820. The components of this novel fluid delivery apparatus generally include a base assembly, an elastomeric membrane serving as a stored energy means, fluid flow channels for filling and delivery, flow control means, a cover, and an ullage which comprises a part of the base assembly.

Another prior art patent issued to one of the present applicants, namely U.S. Pat. No. 5,743,879, discloses an injectable medicament dispenser for use in controllably dispensing fluid medicaments such as insulin, anti-infectives, analgesics, oncolylotics, cardiac drugs, biopharmaceuticals, and the like from a pre-filled container at a uniform rate. The dispenser, which is quite dissimilar in construction and operation from that of the present invention, includes a stored energy source in the form of a compressively deformable, polymeric, elastomeric member that provides the force necessary to controllably discharge the medicament from a pre-filled container, which is housed within the body of the device. After having been deformed, the polymeric, elastomeric member will return to its starting configuration in a highly predictable manner.

Another important prior art fluid delivery device is described in the U.S. Pat. No. 6,063,059 also issued to one of the present inventors. This device, while being of a completely different construction from the device of the present invention, embodies a compressible-expandable stored energy source somewhat similar to that used in the apparatus of the present invention.

As will be appreciated from the discussion which follows, the apparatus of the present invention is uniquely suited to provide precise, continuous fluid delivery management at a low cost in those cases where a variety of precise dosage schemes are of utmost importance. An important aspect of the apparatus of the present invention is the provision of dual reservoirs and novel means for filling the reservoirs with the same or different medicinal agents. One form of the invention includes a pair of rotatable fluid flow rate control means, each of which includes uniquely formed, multichannel flow rate control channels which enable precise control of the rate of fluid flow of the medicaments from either or both of the fluid reservoirs to the patient. More particularly, the apparatus of the present invention includes novel, adjustable fluid flow rate control mechanisms which enable the fluid contained within each of the fluid reservoirs of the device to be precisely dispensed to the patient at various selected rates. The apparatus also includes a reservoir selector means for selecting the reservoir from which the fluid will be removed and delivered to the patient via the flow rate control mechanisms.

Advantageously, the apparatus of the present invention can be used with minimal professional assistance in an alternate health care environment, such as the home. By way of example, devices of the invention can be comfortably and conveniently, removably affixed to the patient's body or clothing and can be used for the continuous infusion of antibiotics, such as, for example, an antibiotic sold by Abbott Laboratories under the name and style ANCIF and by Rosche under the name and style ROCEPHIN. The devices of the invention can also advantageously be used for the delivery of various analgesics such as morphine and like medicinal agents.

Additionally, the apparatus of the invention is useful in the mixing and delivery of various types of adjuvant drugs. Adjuvant therapy, which is additional treatment given after surgery, may include chemotherapy, radiation therapy, hormone therapy, or biological therapy. Adjuvant drugs are generally defined as auxiliary drugs used concurrently with nonopioid or opioid analgesics. Several types of adjuvant drugs play important roles in cancer pain management. Some, such as, laxatives, antiemetics, antinausea drugs, and stimulants, treat symptoms, such as constipation, vomiting, nausea, and sedation that may contribute to pain or develop as a side effect of therapy. Other adjuvant drugs enhance the pain-relieving effects of opioids, or independently provide relief for certain types of pain. Anticonvulsants, for example, can be used with opioids and are prescribed to treat neuropathic pain, especially pain that has an electric shock-like nature. Antidepressants, which are also coanalgesics for opioids, are prescribed for neuropathic pain that is experienced as a hot, burning sensation. Some other commonly prescribed adjuvants are antihistamines, anxiolytics, corticosteroids, local anesthetics and stimulants. Some of the more commonly used adjuvant analgesics include corticosteroids, nonsteriodal anti-inflammatory drugs, tricyclic antidepressants, anticonvulsants and bisphosphonates.

Thromboembolic disease may, by way of example, be treated by chemohormonal therapy using cyclophosphamide, methotrexate, fluorouracil, vincristine, prednisone, doxorubicin and tamoxifen.

The apparatus of the invention is also particularly useful in polychemotherapy which is defined as the use of more than one chemotherapy drug. Such treatment is generally considered to be substantially more effective than using a single agent. Giving more than one medication increases the odds of destroying all the cancer cells and the development of this strategy has accounted for major advances in cancer treatment. Tumors in their early stages grow rapidly because they have a high growth fraction. Over a period of time, as the number of cancer cells grows and the tumor burden increases, the tumor's growth fraction begins to decrease. Cell-cycle specific and cell-cycle non-specific drugs are given in combination, because the cell-cycle specific drugs reduce the tumor growth factor, and cell-cycle non-specific drugs help to reduce the tumor burden. Combination chemotherapy is typically given in courses or cycles. The number of courses varies depending on the type of cancer, the cytotoxic drugs used, and the patient's response to therapy. Combination therapy protocols are usually described by abbreviations that use the first letter of each drug in the protocol. For example, CAF (Cyclophosphamide+Adriamycin+Fluorouracil) is a combination protocol used to treat breast cancer.

There are several advantages of using a combination of drugs rather than a single agent. For example, combining drugs that act in different phases of the cell-cycle increases the number of cells exposed to cytotoxic effects. Similarly, combining drugs decreases the incidence and severity of side effects of therapy and decreases the possibility of drug resistance. Further, combinations of drugs are often effective in patients with large tumors containing a small number of cells that are reproducing. In this instance, one of the drugs kills a high proportion of tumor cells and stimulates the remaining tumor cells to start reproducing. The other drugs in combination therapy can then attack newly reproducing cells.

By way of summary, the apparatus of the present invention uniquely overcomes the drawbacks of the prior art by providing a novel, disposable dispenser of simple, but highly reliable construction. A particularly important aspect of the apparatus of the present invention resides in the provision of novel, self-contained energy sources which are in the form of expandable-retractable spring members that provide the force necessary to selectively and substantially uniformly dispense various solutions from the dual reservoirs of the device. Because of the simplicity of construction of the apparatus of the invention and the straightforward nature and operational reliability of the energy sources, the apparatus can be manufactured and maintained at low cost without in any way sacrificing accuracy and reliability.

SUMMARY OF THE INVENTION

It is an object of the present invention to provide a novel, dual reservoir fluid dispenser for use in controllably dispensing fluid medicaments, such as antibiotics, analgesics, and like medicinal agents from either or both of the device reservoirs.

It is another object of the invention to provide a fluid dispenser of the aforementioned character which is highly reliable and is easy-to-use by laypersons in a non-hospital environment.

Another object of the invention is to provide a small, compact fluid dispenser that includes novel fill means for selectively filling each of the dispenser reservoirs with the same or different medicaments that are to be dispensed to the patient.

Another object of the invention is to provide an apparatus which can be factory pre-filled with a wide variety of medicinal fluids or one which can readily be filled in the field shortly prior to use.

Another object of the invention is to provide a dispenser in which stored energy sources are provided in the form of a pair of constant force spring members of novel design that provide the force necessary to continuously and substantially uniformly expel fluid from the device reservoirs.

Another object of the invention is to provide a device of the aforementioned character which includes novel adjustable flow rate control means disposed intermediate the outlet port of the fluid reservoirs and the outlet port of the device for precisely and selectively controlling the rate of fluid flow from the outlet port toward the patient.

Another object of the invention is to provide a device of the character described which includes reservoir selector means for controlling fluid flow toward the patient from one or both of the fluid reservoirs of the device via the rate control means of the device.

Another object of the invention is to provide a dispenser that includes precise variable flow rate selection from both of the reservoirs of the device.

Another object of the invention is to provide a device of the character described which includes priming means for priming the various fluid passageways of the device and purging the fluid passageways of gases that may be contained therein prior to the delivery of the medicinal fluids to the administration line of the device.

Another object of the invention is to provide a flow rate control device of the aforementioned character in which the flow rate selector member can be locked against rotation by means of a novel locking mechanism once a particular fluidic flow control channel is selected.

Another object of the invention is to provide a fluid dispenser of the class described which is compact, lightweight, is easy for ambulatory patients to use, is fully disposable, and is extremely accurate so as to enable the infusion of precise doses of medicament over prescribed periods of time.

Another object of the invention is to provide a device of the character described which embodies a novel fluid volume indicator that provides a readily discernible visual indication of the volume of fluid remaining within each of the device reservoirs of the device.

Another object of the invention is to provide a self-contained medicament dispenser which is of very simple construction and yet extremely reliable in use.

Another object of the invention is to provide a fluid dispenser as described in the preceding paragraphs which is easy and inexpensive to manufacture in large quantities and may be disposable after use.

BRIEF DESCRIPTION OF THE DRAWINGS

FIG. 2 is a top plan view of the device shown in FIG. 1.

FIG. 3 is a side-elevational view of the device shown in FIG. 1.

FIG. 4 is an enlarged cross-sectional view taken along lines 4-4 of FIG. 3.

FIG. 5 is a cross-sectional view taken along lines 5-5 of FIG. 4.

FIG. 6A is an enlarged, fragmentary cross-sectional view of a portion of the bellows reservoir wall of one form of the invention.

FIG. 7A is a fragmentary, cross-sectional view of the forward portion of the device shown in FIG. 7 showing in greater detail the coupling of the fill means of the apparatus within the dispenser portion of the apparatus.

FIG. 10 is a longitudinal cross-sectional, exploded view of one form of the fill means of the apparatus of the invention showing the fill vial portion of the fill means in position to be mated with the body portion of the fill means.

FIG. 11 is a longitudinal cross-sectional view similar to FIG. 10, but showing the fill vial portion of the fill means having been mated with the body portion thereof.

FIG. 12 is an enlarged, cross-sectional, exploded view of the portion of the apparatus designated in FIG. 4 by the numeral 13.

FIG. 12A is a greatly enlarged cross-sectional view of one of the fluidic micro channels of the flow control means of the invention.

FIG. 13 is a view taken along lines 13-13 of FIG. 12.

FIG. 13A is a cross-sectional view taken along lines 13A-13A of FIG. 12.

FIG. 13B is a cross-sectional view taken along lines 13B-13B of FIG. 12.

FIG. 14 is a top plan view of one of the first and second identical flow rate control members of the flow control means of one form of the invention.

FIG. 15 is a view taken along lines 15-15 of FIG. 14.

FIG. 16 is a bottom plan view of one of the first and second identical flow rate control members of the flow control means of one form of the invention.

FIG. 17 is a view taken along lines 17-17 of FIG. 16.

FIG. 18 is a top plan view of one of the first and second identical upper rate control housings of the flow control means of one form of the invention.

FIG. 19 is a view taken along lines 19-19 of FIG. 18.

FIG. 20 is a top plan view of one of the first and second identical lower rate control housings of the flow control means of one form of the invention.

FIG. 21 is a view taken along lines 21-21 of FIG. 20.

FIG. 22 is a generally perspective, diagrammatic view illustrating the fluid flow path from one of the fill means of the apparatus of the invention toward one of the fluid reservoirs of the device.

FIG. 23 is a fragmentary, longitudinal cross-sectional, diagrammatic view further illustrating the fluid flow path from one of the fill means of the apparatus of the invention toward one of the fluid reservoirs of the device.

FIG. 27 is a generally tabular view illustrating the fluidic properties of one form of the fluid rate control member, or rate control chip of the form of the flow rate control device shown in FIG. 26.

DESCRIPTION OF THE INVENTION

Figure 1:
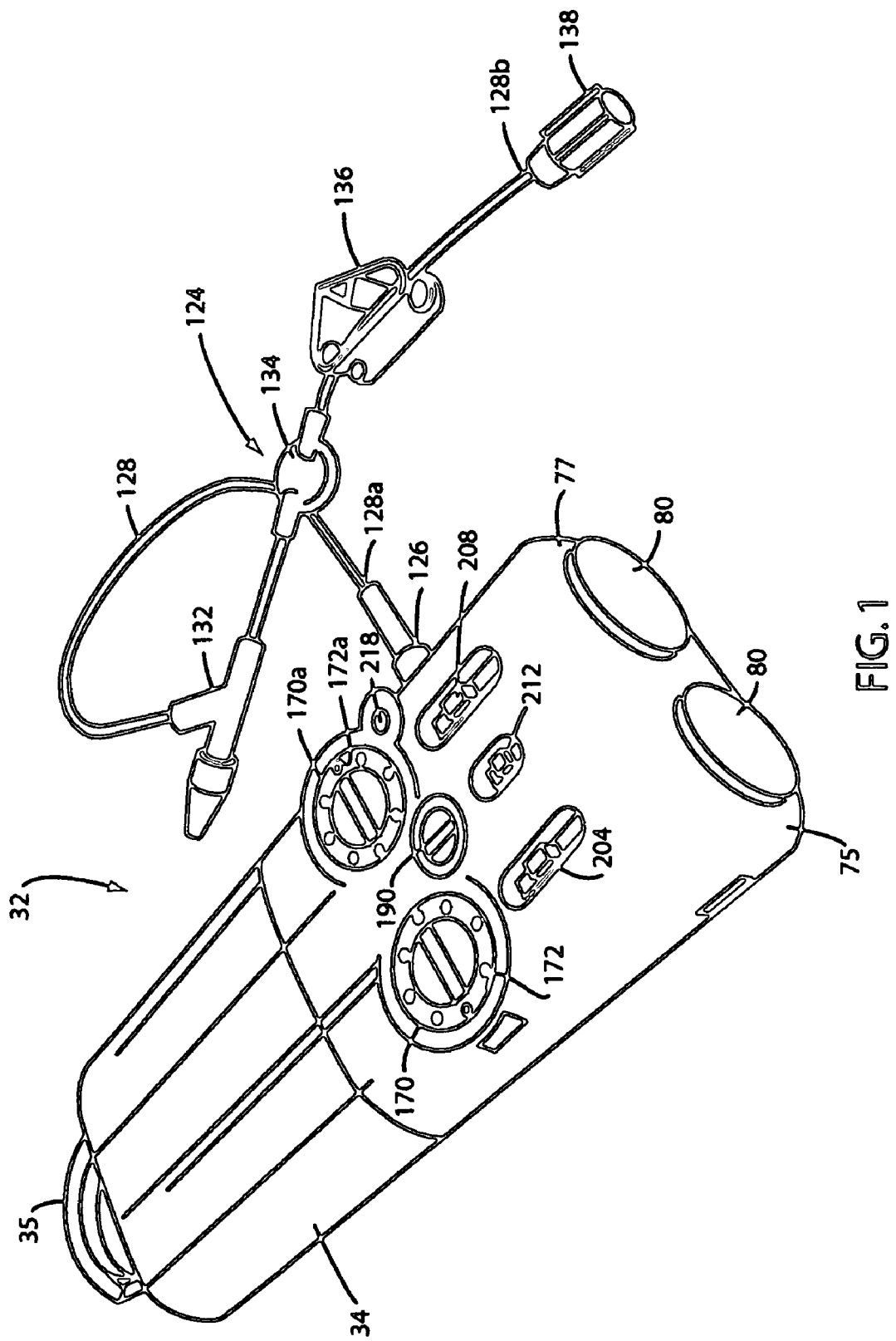
FIG. 1 is a generally perspective view of one form of the fluid delivery device of the present invention.
Figure 6:
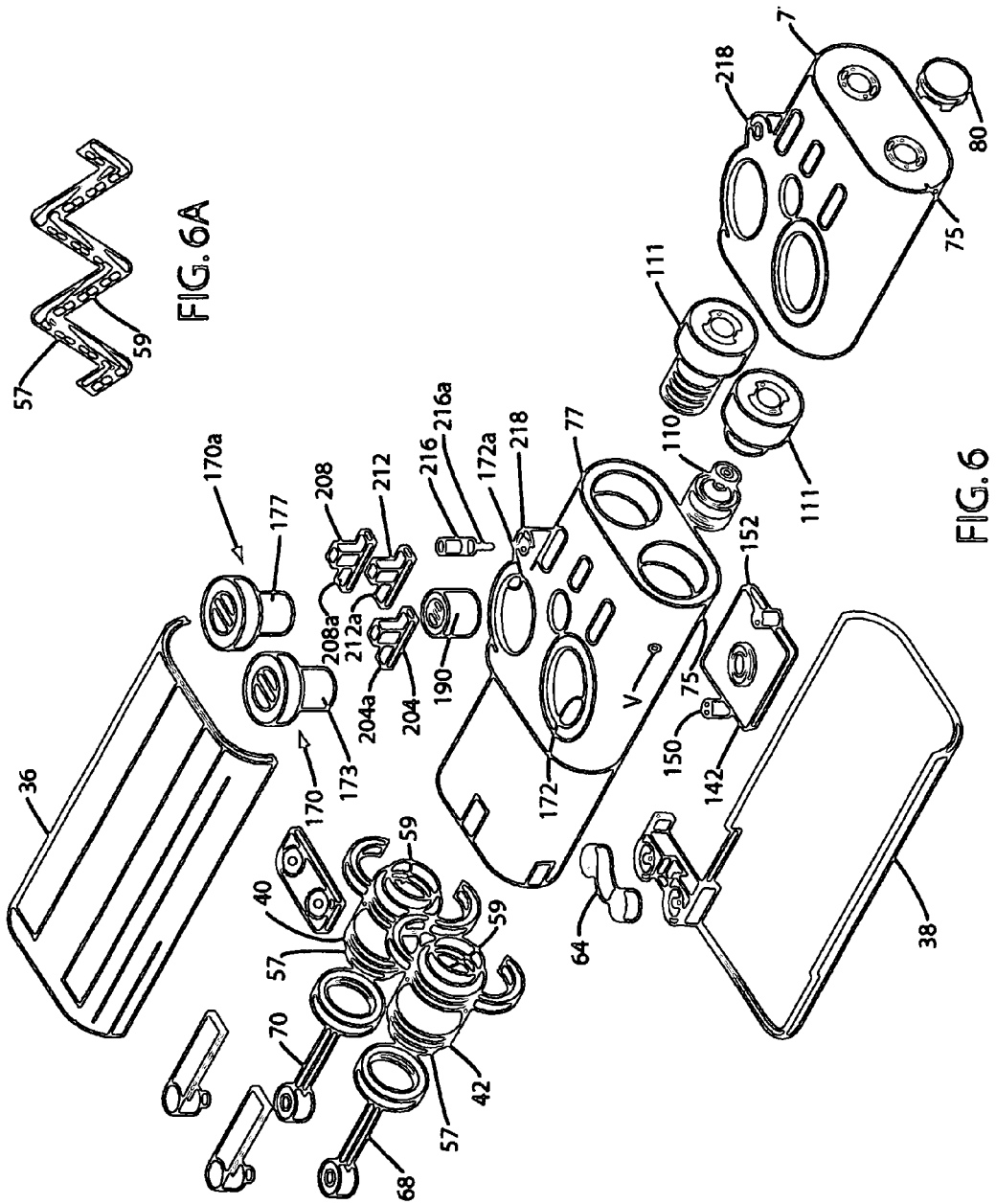
FIG. 6 is a generally perspective exploded view of the device shown in FIGS. 4 and 5.
Figure 7:
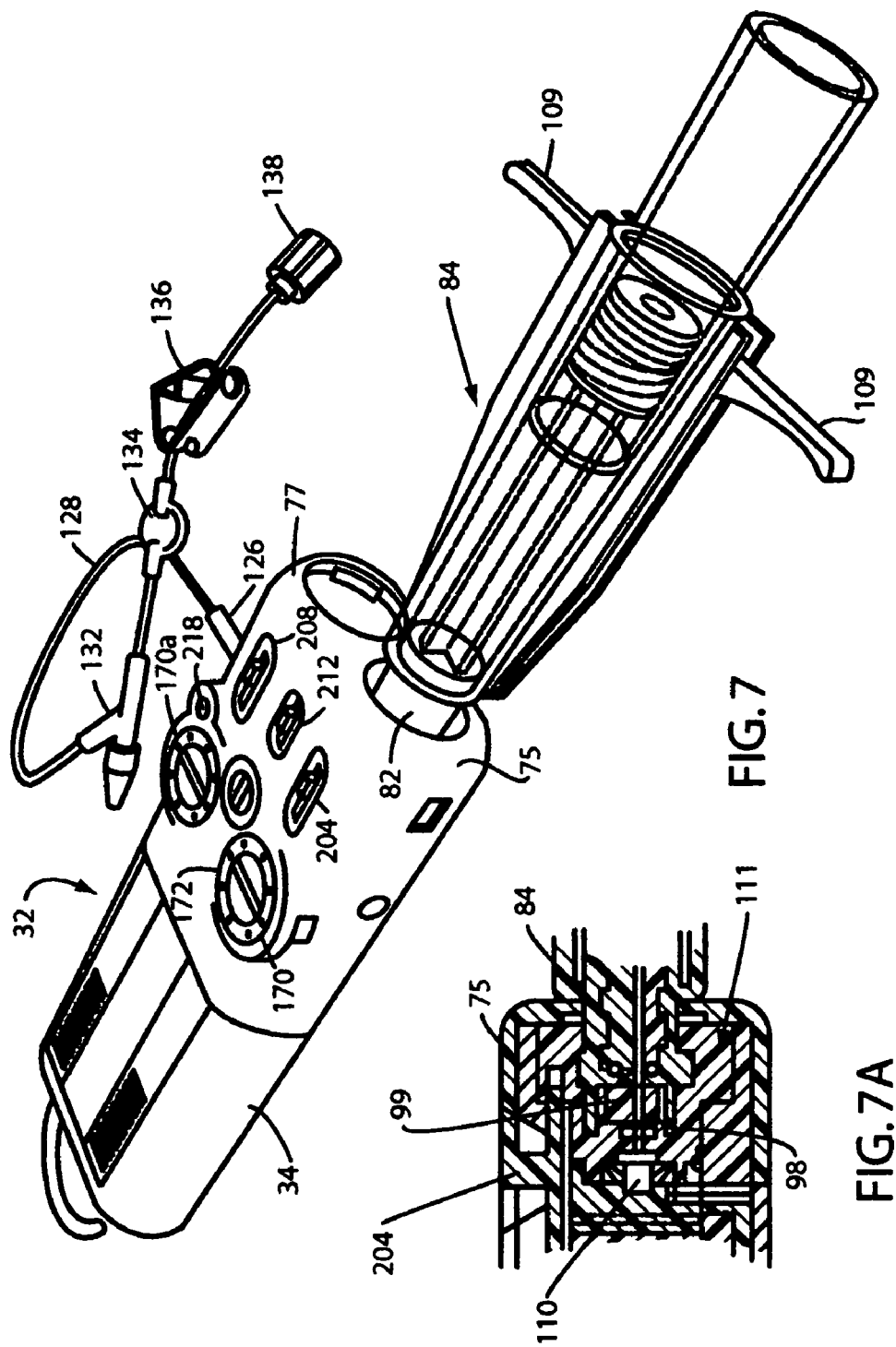
FIG. 7 is a generally perspective view of the device shown in FIG. 1 coupled with one form of the fill means of the apparatus of the invention for filling one of the fluid reservoirs of the apparatus.

Referring to the drawings and particularly to FIGS. 1 through 6, one embodiment of the fluid dispensing apparatus of the present invention is there illustrated and generally designated by the numeral 32. As best seen in FIGS. 1 and 6, the apparatus here comprises a snap-together plastic outer housing 34 having a support hook 35 and first and second portions 36 and 38 respectively. Disposed within outer housing 34 are first and second expandable housings 40 and 42. Expandable housing 40 has a fluid reservoir 44 provided with an inlet 46 (FIG. 4) for permitting fluid flow into the fluid reservoir and an outlet 48 for permitting fluid flow from the fluid reservoir. Similarly, expandable housing 42 has a fluid reservoir 50 provided with an inlet 52 (FIG. 4) for permitting fluid flow into the fluid reservoir and an outlet 54 for permitting fluid flow from the fluid reservoir.

Expandable housings 40 and 42, which can be constructed from a metal or plastic material, each comprise a closed in flexible bellows structure having an expandable and compressible, accordion-like, annular-shaped sidewall 57, and an end wall 57a which is interconnected with the side wall when the bellows structure is in position with the device housing, the open end thereof is sealably closed to define a dynamic sealed reservoir the configuration of which is best seen in FIGS. 4, 6 and 6A. If the internal materials interface of the bellows structure and other fluid channels or surfaces is not sufficiently compatible with the planned beneficial agent to be delivered, either in terms of its biocompatibility or drug up-take characteristics, application of a surface modification process is appropriate. This surface modification methodology may take one of several forms. One process that is extremely clean, fast and efficient is plasma processing. In particular, this technique allows for plasma activation, plasma-induced grafting and plasma polymerization of molecular entities on the internal drug surface of the bellows. For cases where an inert hydrophobic interface is desired, plasmas using fluorine-containing molecules may be employed. In this regard, the coated bellows surface 59 (FIG. 6A), as well as other surfaces that may be contacted by the beneficial agent may be cleaned with an inert gas plasma, and subsequently, a fluorine-containing plasma may be used to graft these molecules to the surface. Alternatively, if a hydrophilic surface is desired (e.g., for drug solutions that are highly corrosive or in oil-based solvents) an initial plasma cleaning may be done, followed by a plasma polymerization using hydrophilic monomers.

Also disposed within housing 34 is the novel stored energy means of the invention for acting upon expandable housings 40 and 42 in a manner to controllably collapse the expandable housings so as to cause the fluid contained within fluid reservoirs 44 and 50 to controllably flow outwardly of the housing. In the present form of the invention, this important stored energy means comprises first and second identically configured constant force springs 62 and 64. Springs 62 and 64 are first extended by fluid flowing into reservoirs 44 and 50 and then controllably retracted to cause fluid flow from the reservoirs, through the flow rate control and dispensing means of the invention and toward the patient. Stored energy means, or constant force springs 62 and 64, which are a special variety of extension springs, are readily commercially available from several sources including Barnes Group Inc. of Bristol, Conn., Stock Drive Products/Sterling Instrument of Hyde Park, N.Y. and Walker Corporation of Ontario, Calif. The constant force extension springs are basically high stress, long deflection devices that offer great advantages when used in applications where very low or zero gradient is desired, where space is a factor and where very high reliability is required. Constant force springs, such as spring 62 and 64, provide markedly superior constant force loading when compared to conventional helical extension or like springs. Springs 62 and 64, which act on pusher members 68 and 70 respectively, are of the character shown in FIGS. 4 and 6 and each can be constructed from stainless steel.

Figure 8:
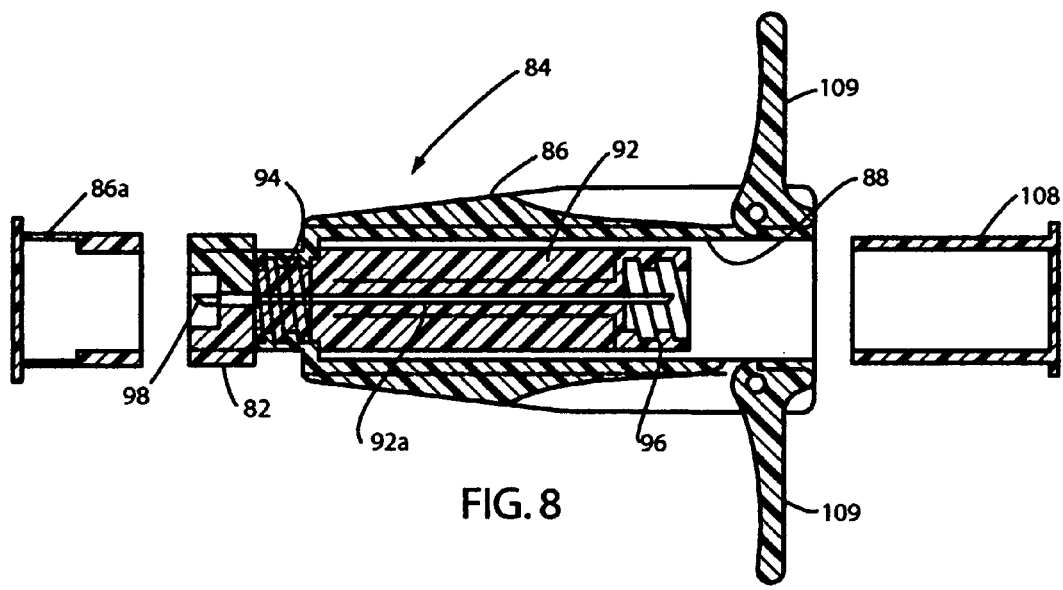
FIG. 8 is a longitudinal, cross-sectional, exploded view of the body portion of the fill means of the apparatus shown in FIG. 7.
Figure 9:
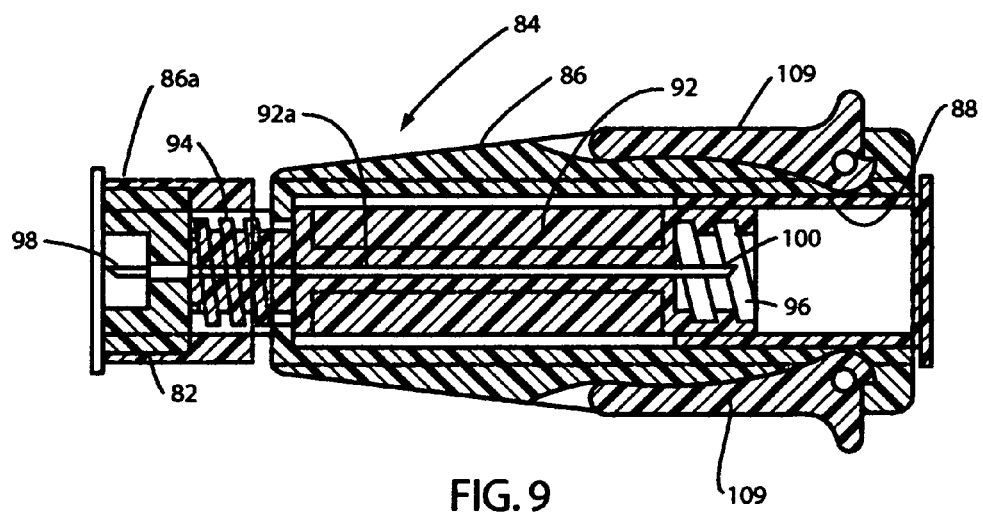
FIG. 9 is a longitudinal cross-sectional view of the body portion of the fill means of the apparatus shown in FIG. 8 with the finger engaging arms of the fill means in a retracted position.

Forming an important aspect of the apparatus of the present invention is fill means which can be aseptically interconnected to housing 34 via a sterile coupling 111 for filling the reservoirs with the fluid to be dispensed. In this regard, as indicated in FIGS. 1, 4 and 6, housing 34 includes first and second connector portions 75 and 77 that are normally closed by identical closure caps 80. These connector portions are adapted to receive the connector portions 82 of the identical fill assemblies 84 of the invention, which are of the construction shown in FIGS. 7 through 11. As shown in FIGS. 8 and 9, each of the fill assemblies 84 includes a hollow housing 86 that is provided with a chamber 88 for telescopically receiving a medicament containing fill vial 90 (FIG. 10), the construction of which will presently be described.

An elongated support 92, which is disposed within chamber 88 of each of the fill assemblies 84, includes threaded end portions 94 and 96 and a central flow passageway 92a. Support 92 carries at one end a hollow needle 98 having a flow passageway which communicates, via passageway 92a with the flow passageway of a second needle or cannula 100 that is carried interiorly of threaded end portion 96 (FIG. 9). Chambers 88, elongated supports 92 and hollow needles 98 and 100 comprise a part of the fill means of the apparatus of the invention for filling reservoirs 44 and 50.

Referring particularly to FIG. 10, the medicament containing fill vial 90 of this form of the invention includes a body portion 90a, having a fluid chamber 104 for containing the injectable fluid medicament. Chamber 104 is provided with a first open end 104a and second closed end 104b. First open end 104a is sealably closed by closure means, here provided in the form of an externally threaded elastomeric plunger 106, which is telescopically movable within chamber 104 from a first location where the plunger is disposed proximate first open end 104a to the second, device-fill location where the plunger is disposed proximate second closed end 104b.

A number of beneficial agents can be contained within vial 90, including by way of example, medicaments of various types, drugs, pharmaceuticals, hormones, antibodies, biologically active materials, elements, chemical compounds, or any other suitable material useful in diagnostic cure, medication, treatment or prevention of diseases or the maintenance of the good health of the patient.

After removal of a closure member 108 from the syringe assembly in the manner shown in FIG. 8, vial 90 can be inserted into chamber 88 (FIG. 11). As the fill vial is so introduced and the plunger 106 is threadably interconnected with threaded end 96 of support 92, the sharp end of the elongated needle 100 will pierce the central wall 106a of the elastomeric plunger in the manner shown in FIG. 11. Following removal of cover members 80 which cover the connector portions of the housing, the syringe assemblies can be mated with the fluid dispenser in the manner shown in FIG. 7. This done, and in preparation for the reservoir filling step, the gripping fingers 109 can be retracted from the retracted position shown in FIG. 9 to the extended position shown in FIG. 8.

During the filling step, reservoirs 44 and 50 are filled in a similar manner. More particularly, with the forward covers 86a of the syringe fill assemblies of the invention removed and with the syringe fill assemblies mated with the connector assemblies 111 of fluid dispenser in the manner indicated in FIG. 7, cannulas 98 will pierce the septums 99 which are mounted within the connector assemblies 111 (FIG. 4). This done, the caregiver grips the retracted fingers 109 of the syringe fill assembly with his or her fingers and exerts an inward pressure on a selected vial 90 causing the vial to move inwardly of chamber 88. A continuous movement of the vial into chamber 88 will cause the structural support 92 to move the elastomeric plunger inwardly of the vial chamber 104 in a direction toward the second, or closed end 104b of the vial chamber. As the plunger is moved inwardly of the vial, the fluid "F" (FIG. 11) contained within the vial chamber will be expelled therefrom into the hollow needle 100. The fluid will then flow into hollow needle 98 and then past the conventional umbrella-type check valves 110 which are mounted within the housing 34 in the manner shown in FIG. 4. When reservoir 44 is being filled, the fluid will flow into a passageway 112 formed in the first rate control means of the invention and then into passageway 114. From passageway 114 the fluid will flow into reservoir 44. When reservoir 50 is being filled, the fluid will flow into a passageway 116 formed in the second rate control means of the invention (FIG. 23) and then into passageway 186. From passageway 186 the fluid will flow into reservoir 50.

As the fluid flows into reservoir 44, it will exert an inward pressure on the plunger end portion 68a of pusher member 68 causing it to move rearwardly of chamber 44. As the pusher member moves rearwardly of chamber 44 it will exert forces on spring member 62 causing it to expand from its retracted configuration shown in the solid lines in FIG. 4 to its expanded configuration shown by the phantom lines in FIG. 4. This rearward movement of pusher member 68 can be viewed through a volume indicator window 115 indicating that the reservoir has changed from an empty configuration to a filled configuration (FIG. 2).

As the fluid flows into reservoir 50, it will exert an inward pressure on the plunger end portion 70a of pusher member 70 causing it to move rearwardly of chamber 50. As the pusher member moves rearwardly of chamber 50 it will exert forces on spring member 64 causing it to expand from its retracted configuration shown in the solid lines in FIG. 4 to its expanded configuration shown by the phantom lines in FIG. 4. This rearward movement of pusher member 70 can be viewed through a volume indicator window 117 indicating that the reservoir has changed from an empty configuration to a filled configuration (FIG. 2). Reservoir volume indicator means in the form of indicia 115a and 117a provide a visual indicator of the level of the fluid content of the reservoirs.

As the reservoirs fill with fluid, any gases trapped within the reservoirs will be vented via a passageway 120a to atmosphere via vent means "V" mounted in the sides of the housing. This vent means here comprises a gas vent 120 that can be constructed of a suitable hydrophobic porous material such as a porous plastic.

Upon opening the fluid delivery path, in a manner presently to be described, a selected one of the stored energy means, or springs 62 and 64, will tend to return to its starting configuration thereby controllably urging fluid flow outwardly of the reservoir with which it is associated. The fluid will then flow, via the flow control means of the invention, into the delivery means of the invention, shown here as a conventional administration set 124 (FIG. 1). Administration set 124 is connected to housing 34 by a connector 126 in the manner shown in FIG. 1 of the drawings. The proximal end 128a of administration line 128 of the administration set is in communication with an outlet fluid passageway 130 which is formed in the housing in the manner best seen in FIG. 4. Disposed between the proximal end 128a and the distal end 128b of the administration line is a conventional Y-site 132 for secondary infusion, a conventional gas vent and filter 134 and a conventional line clamp 136. Provided at the distal end 128b of the administration line is a luer connector 138 of conventional construction (FIG. 1).

As the fluid contained within reservoirs 44 and 50 is urged outwardly thereof by the stored energy means associated with the reservoirs, the fluid will flow under pressure through the outlet of the reservoirs and then on toward the first and second flow control means of the invention that are associated with the reservoirs. This important flow control means functions to precisely control the rate of fluid flow flowing from a particular reservoir toward the patient.

Turning to FIGS. 12 through 21, the details of construction of one of the identical first and second rate control assemblies of the flow control means of the invention is there shown. This rate control assembly, which is generally identified by the numeral 142 (FIG. 12), here comprises a housing 144 having an upper portion 144a and a lower portion 144b. Disposed between the upper and lower housing portions is the important rate control plate 146 of the invention (see FIGS. 12 and 14-17).

As best seen in FIG. 12, the rate control assembly 142 includes an inlet port 150 that is in communication with the outlet port of one of the reservoirs and an outlet port 152 that is in communication with administration set 124 via the selector means of the invention, the character of which will presently be described. As illustrated in FIG. 16, rate control plate 146 is provided with a plurality of fluidic micro channels identified as 155, 157, 159, 161, 163, 165 and 167, each of which has an inlet in communication with inlet port 150 of housing 144 via a filter means, or filter "F" for filtering fluid flowing towards the micro channels (FIG. 26) and an outlet that, in a manner presently to be described, can selectively communicate with the inlet of one of the identical first and second selector means of the invention. It is to be understood that the micro channels may be of different sizes, lengths, widths, depths and configurations as shown by FIG. 16. Further, the flow control micro channels may be rectangular in cross section, or alternatively, they can be semicircular in cross section, U-shaped in cross section, or they may have any other cross-sectional configuration that may be appropriate to achieve the desired fluid flow characteristics.

The details of the construction of the rate control plate 146 and the various methods of making the rate control plate will now be considered. With respect to materials, the most appropriate materials for constructing the rate control plate are medical grade polymers. These types of polymers include thermoplastics, duroplastics, elastomers, polyurethanes, acrylics and epoxies. In other variations, the materials used for the flow control plate may be made of glass, or silica, silicon and various types of plastics. In further variations, the flow control component may be made of metals or inorganic oxides.

Using the foregoing materials, there are several ways that the flow control channels can be made. These include injection molding, injection-compression molding, hot embossing, laser ablation and casting. The techniques used to make these imbedded fluid channels are now commonplace in the field of microfluidics, which gave rise to the lab-on-a-chip, bio-MEMS and micro-total analysis systems (μ-TAS) industries. Additionally, depending on the size of the fluid channels required for a given flow rate, more conventional injection molding techniques can be used.

The first step in making the channels using an injection molding or embossing process is a lithographic step, which allows a precise pattern of channels to be printed on a "master" with lateral structure sizes down to 0.5 μm. Subsequently, electroforming is performed to produce the negative metal form, or mold insert. Alternatively for larger channel systems, precision milling can be used to make the mold insert directly. Typical materials for the mold insert or embossing tool are nickel, nickel alloys, steel and brass. Once the mold insert is fabricated, the polymer of choice may be injection molded or embossed to yield the desired part with imprinted channels.

Alternatively, channels can be made by one of a variety of casting processes. In general, a liquid plastic resin, for example, a photopolymer can be applied to the surface of a metal master made by the techniques described in the preceding paragraph and then cured via thermal or ultraviolet (UV) means. After hardening, the material is then "released" from the mold to yield the desired part. Additionally, there are similar techniques available that utilize CAD data of the desired channel configuration and direct laser curing of a liquid monomer to yield a polymerized and solidified part with imbedded channels. This process is available by contract, from, by way of example, example MicroTEC, GmbH of Duisburg, Germany.

In order to seal the flow control channels, a planar top plate may be used. In this instance, the channel system may be sealed with a top plate, which is here defined as any type of suitable cover that functions to seal the channel. The top plate may be sealably interconnected with the base plate which contains the flow channels by several means, including thermal bonding, sonic welding, laser welding, adhesive bonding and vacuum application.

Thermal bonding may be performed by using a channel base plate material and planar top cover that are made of similar polymeric materials. In this case the two substrates are placed in contact with one another, confined mechanically and heated to 2-5° C. above their glass transition temperature. Following a holding period sufficient enough for the polymer molecules of the two surfaces to interpenetrate with one another, the temperature is slowly reduced and a stress-free bonded interface with imbedded micro channels is yielded.

Additionally, the top plate may be bonded to the base plate through the use of one or more suitable bonding materials or adhesives. The bonding material or adhesive may be of the thermo-melting variety or of the liquid or light-curable variety. For thermo-melting adhesives, the adhesive material is melted into the two opposed surfaces, thereby interpenetrating these surfaces and creating a sealed channel structure.

Further, liquid-curable bonding materials or adhesives and light-curable bonding materials or adhesives may be applied to one of the surfaces, for example the top plate. Subsequently, the other surface is brought into contact with the coated surface and the adhesive is cured by air exposure or via irradiation with a light source. Liquid-curable bonding materials or adhesives may be elastomeric, for example, thermoplastic elastomers, natural or synthetic rubbers, polyurethanes, and silicones. Elastomeric bonding materials may or may not require pressure to seal the channel system. They may also provided closure and sealing to small irregularities in the opposed surfaces of the channel system.

A channel system may also be formed and sealed in cases where two surfaces are being joined and one of the surfaces has one or more apertures. In order to promote bonding between these two surfaces, a vacuum may be applied to the apertures. Bonding may then be accomplished by thermal methods or after previously having applied a bonding material or adhesive.

While the rate control plate can be constructed in various sizes, a rate control chip which is rectangular in shape and approximately 11 cm long and approximately 5 cm wide is suitable for the present application. Similarly, while the depth of the channels can vary depending upon the end use of the device, as a general rule the depth of the channels is on the order of approximately 1-1000 p.m.

As previously mentioned, the cross section of the set of channels may vary in area over the members of the set of individual channels so as to achieve the specified flow rate of a particular channel. The cross section may also vary over the length of any particular channel so as to achieve the specified flow rate for the particular channel. Some examples of typical channel cross sections are square, rectangular, elliptical, circular, semi-circular and semi-elliptical. Channel cross sections may also be more complicated than those noted explicitly here.

A typical chip will be able to deliver fluid at five specified flow rates as, for example 0.25, 0.5, 1.0, 2.0, 5.0 and greater ml/hr. for optimum performance, the flow rate should be constant and within 10% of the desired specified value at room temperature.

In operation of the apparatus of the invention, the flow of fluid through the flow control channels is controlled by taking advantage of the viscous drag imposed on the moving fluid by the walls of the channels. For a given imposed pressure and channel cross section, the longer the channel the smaller the flow rate. The pressure required to achieve the desired flow rates in the micro channels is preferably in the range of from 0.01 to 1 ATM. However, for some applications it may be desirable to exceed these limits.

The path that the micro channels take in any given rate control plate may be straight, a single meander or two or more meanders. The turns of the meanders may be of any angle from approximately 45° to approximately 220°. The runs of straight path between turns of the meanders may be of any length that the chip can accommodate, but these straight runs would typically be from 50 μm to 500 μm in length.

Figures 24, 25:
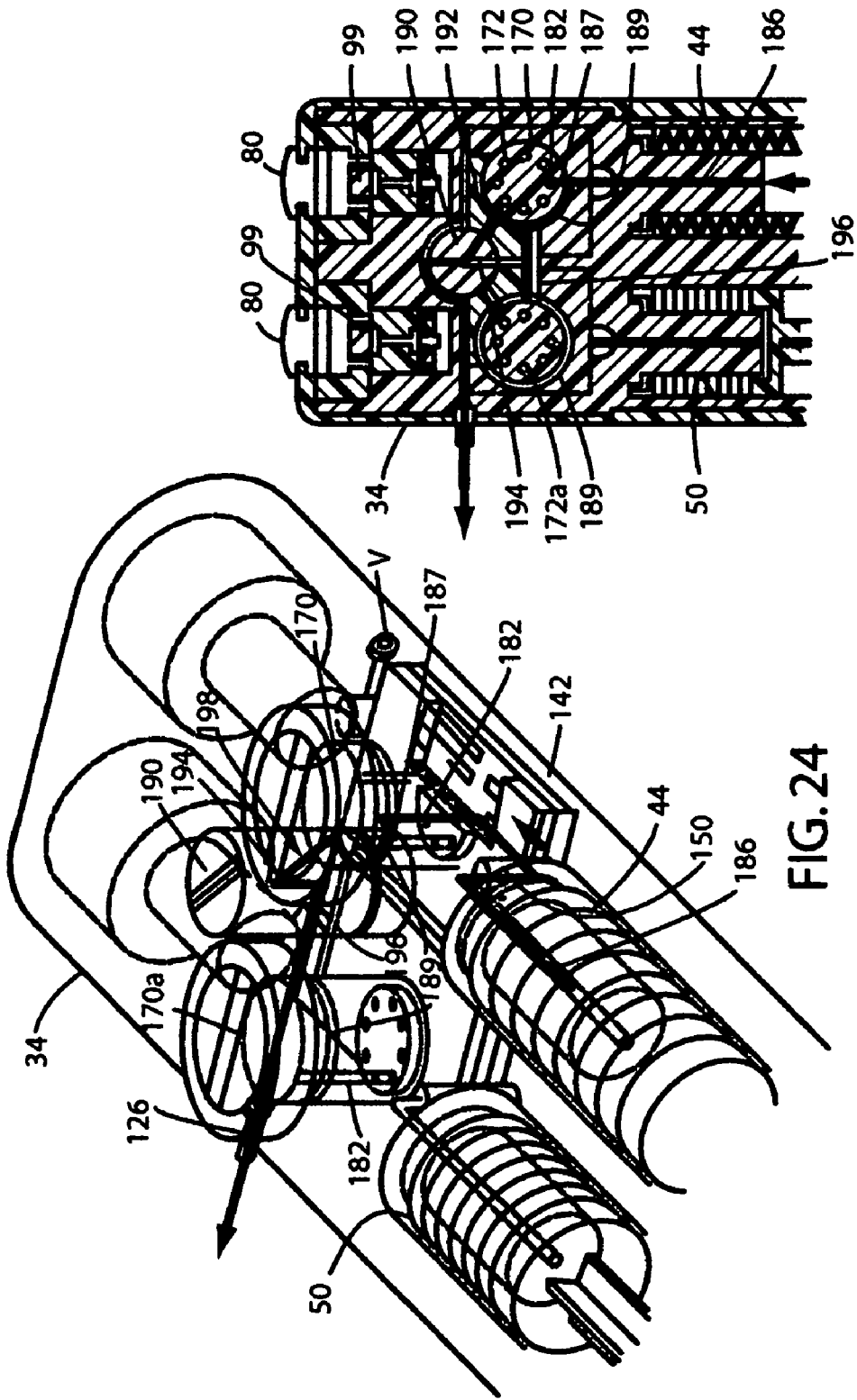
FIG. 24 is a generally perspective, diagrammatic view illustrating the fluid flow path from one of the fluid reservoirs of the apparatus of the invention outwardly of the device toward the patient.
FIG. 25 is a fragmentary, longitudinal cross-sectional, diagrammatic view further illustrating the fluid flow path from one of the fluid reservoirs of the apparatus of the invention outwardly of the device toward the patient.

After the reservoirs have been filled with the appropriate fluids in the manner illustrated in FIGS. 22 and 23, either of the fluids contained within the reservoirs, or a mixture of the fluids can be delivered to the patient at a precise rate. The rate of fluid delivery to the patient is selected by controllably rotating the selector knobs 170 and 170a within their respective vertical bores 172 and 172a. Such rotation will permit the passageways 182, which are formed within each of the selector knobs (FIG. 12), to be moved into alignment with a selected one of the circumferentially-spaced outlet ports of the rate control plate 146 with which the knob is associated. Referring particularly to FIGS. 4 and 24, and by way of example, during the delivery of fluid contained within reservoir 44 of the apparatus to the patient via the administration set 124, as the pusher assembly 68 is urged forwardly by the stored energy means, or spring 62, the medicinal fluid contained within reservoir 44 will flow through reservoir outlet port 48, through a passageway 186 formed in the device housing and into inlet 150 of rate control assembly 142 (see FIG. 4). As the fluid flows into inlet 150, each of the micro channels of the rate control plate 146 will fill with the medicinal fluid. When the selector knob 170 is then rotated to a position wherein passageway 182 of the selector knob is aligned with the outlet of one of the micro channels of the rate control plate 146, fluid will flow from that micro channel into passageway 182, then into passageway 187 which is in communication therewith and then into an annular passageway 189 which is in communication with passageway 187 (see FIGS. 24 and 25). Delivery of fluid to the patient from second reservoir 50 of the apparatus is accomplished in a similar manner through rotation of selector member, or knob 170a within bore 172a to align passageway 186 of this selector knob with one of the micro channels of the rate control plate with which knob 170a is associated.

From passageways 189 of the selector knob, the fluid will flow toward the third, or reservoir selector member 190 via a passageway 192 formed in the apparatus housing. Reservoir selector member 190 functions to control fluid flow from either or both of the rate control assemblies toward the patient via administration set 124. From passageways 192, the fluid will flow into a connector passageway 194, which is formed within reservoir selector member 190 and which functions to permit fluid flow from either of the annular passageways 189 formed in the selector knobs or from a cross-connect passageway 196 formed in the device housing (FIG. 24), which interconnects the annular flow passageways 189 of selector knobs 170 and 170a (see also FIGS. 13, 24 and 25). In a manner presently to be described, this permits fluid flow toward the patient from a selected one of the fluid reservoirs 44 and 50, or alternatively simultaneously from both of the reservoirs via reservoir selector member 190.

As illustrated in FIG. 13 of the drawings, reservoir selector member 190 is rotatable within a bore 197 formed within the device housing into three positions. In a position shown in FIG. 13 the reservoir selector member will permit fluid flow from passageway 196, which passageway is in fluid communication with both reservoirs 44 and 50 via a passageway 199 formed in the device housing. If the reservoir selector member is rotated in a clockwise direction from the position shown in FIG. 13, fluid will be permitted to flow from reservoir 50 toward the patient via a passageway 201. Similarly, if the reservoir selector member is rotated in a counter clockwise direction from the position shown in FIG. 13, fluid will be permitted to flow from reservoir 44 toward the patient via a passageway 192.

Also forming a part of the flow control means of the invention is selector knob-locking means for preventing rotation selector knobs 170 and 170a. This selector knob-locking means here comprises a first locking member 204 that is slidably carried by the device housing for movement between a first locking position wherein the locking finger 204a of the member is received within a locking slot 206 formed in the periphery of selector knob 170 (See FIG. 13A) and a second retracted position wherein the locking finger is retracted from the locking slot. The knob-locking means further comprises a second locking member 208 that is slidably carried by the device housing for movement between a first locking position wherein the locking finger 208a of the member is received within a locking slot 206 formed in the periphery of selector knob 170a and a second retracted position wherein the locking finger is retracted from the locking slot (see FIGS. 6 and 13).

The flow control means of the invention further includes a reservoir selector knob-locking means for preventing rotation of reservoir selector member 190. This locking means is similar in construction to the selector knob-locking means and comprises a locking member 212 that is slidably carried by the device housing for movement between a first locking position wherein the locking finger 212a of the member is received within a locking slot 214 formed in the periphery of reservoir selector member 190 (see FIG. 13B).

In light of the foregoing discussion, it is apparent that by rotation of selected knobs 170 and 170a the rate of fluid flow from each of the device reservoirs toward the administration line can be precisely controlled. Similarly, by rotation of the reservoir selector knob 190, the flow of fluid toward the administration line can be from either of the reservoirs or simultaneously from both of the reservoirs. The delivery status of the reservoirs can be continuously monitored by referring to the volume indicator windows 115 and 117.

If at any time it is desired to disable the device and render it inert, disable means are provided in the form of a disabling member 216 (FIG. 6) that includes a disabling shaft 216a that will block fluid flow through outlet fluid passageway 130 (FIG. 4) when the disabling member is urged downwardly within a cavity 218 formed in the device housing causing shaft 216a to intersect and block passageway 130.

Figure 26:
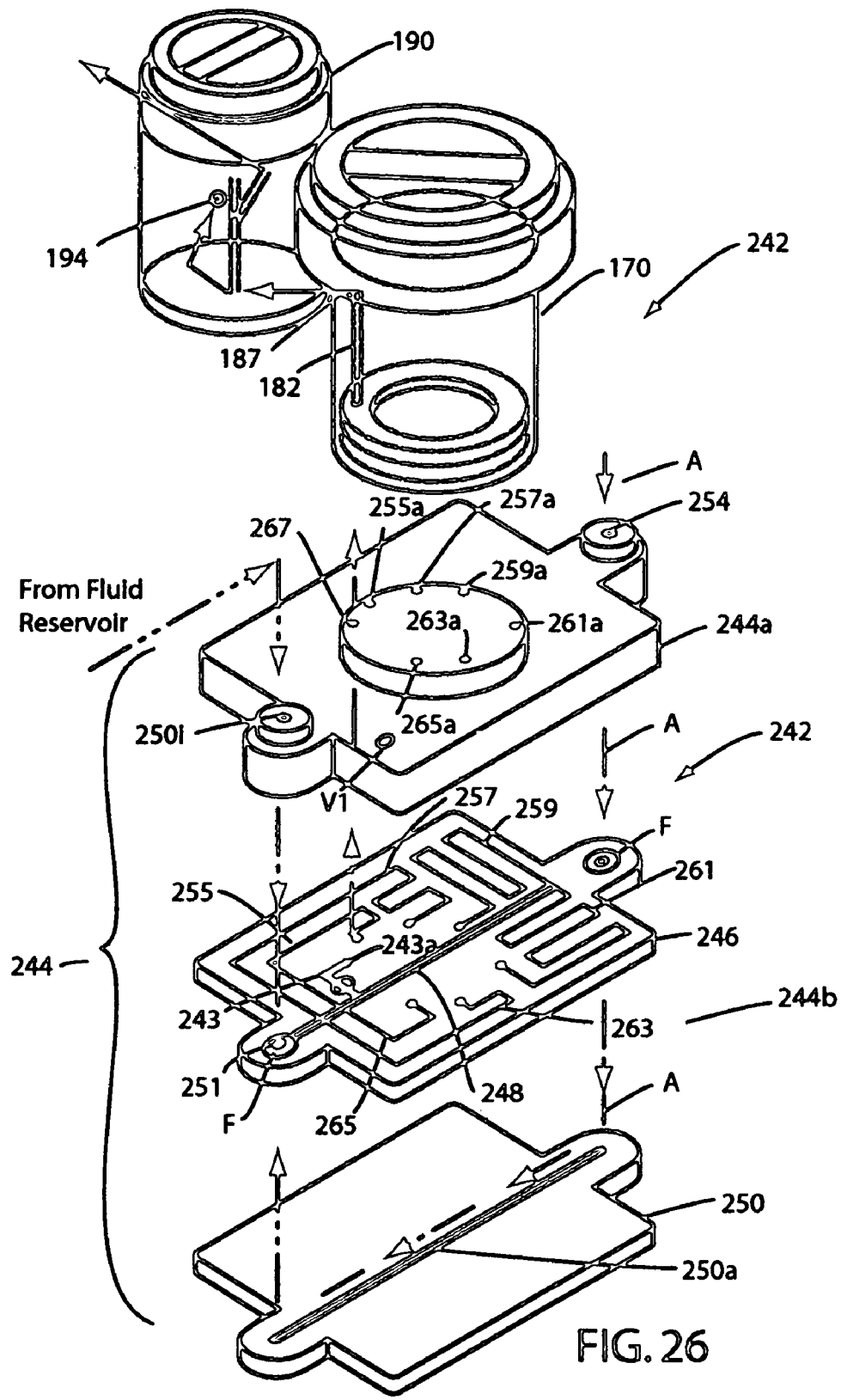
FIG. 26 is a generally perspective, exploded view illustrating a portion of an alternate form of flow control means of the invention, which includes priming means for priming the various fluid passageways of the device prior to delivery of fluid to the administration set.

Turning next to FIG. 26, an alternate form of flow control means of the invention is there shown. This alternate form of flow control means is similar in many respects to the device shown in FIGS. 12 through 21 and like numerals are used in FIG. 26 to identify like components. A primary difference between the flow control means of this latest form of the invention and the earlier described flow control means resides in the provision of identical first and second rate control assemblies which uniquely include priming means for priming the various fluid passageways of the device prior to delivery of fluid to the administration set.

One of the identical first and second rate control assemblies of this latest form of the invention is illustrated in a lower portion of FIG. 26 and is generally designated by the numeral 242. This rate control assembly is housed within plastic outer housing 34 of the apparatus in the same manner as the earlier described first and second rate control assemblies of the first embodiment of the invention. Rate control assembly 242 here comprises a housing 244 having an upper portion 244a and a lower portion 244b. Disposed between the upper and lower housing portions is the important rate control plate 246 of the invention which includes a prime channel 248 that comprises a part of the priming means of this latest form of the invention. Rate control plate 246, which is superimposed over a bottom plate 250 in the manner indicated in FIG. 26, includes a flow passageway 250a the purpose of which will presently be described.

As illustrated in FIG. 26, the rate control assembly 242 includes an inlet port 251 that is in communication with the outlet port of one of the reservoirs 44 and 50. The reservoirs are, in turn, in communication with the syringe fill assemblies of the invention, which are identical in construction and operation to those previously described. The reservoirs 44 and 50 of the device are filled by the syringe fill assemblies in substantially the same manner as earlier described herein. In this regard, when the reservoirs are being filled, fluid will flow past the check valves 110 which are mounted within housing 34, then into the inlet 244b of upper portion 244a of the rate control housing and finally, in the direction of the arrows "A" of FIG. 26, into the passageways 250a formed in base plates 250.

As in the first described embodiment of the invention, rate control plate 246 is provided with a plurality of fluidic micro channels, here identified as 255, 257, 259, 261, 263 and 265, each of which has an inlet in communication with the prime channel 248 via filter "F" and an outlet that can selectively communicate with the inlet of one of the identical first and second selector means of this latest form of the invention, only one of which is shown in the upper portion of FIG. 26. As before, the micro channels may be of different sizes, lengths, depths, widths and configurations as shown by FIG. 26. Further, the flow control micro channels may be rectangular in cross section, or alternatively, they can be semicircular in cross section, U-shaped in cross section, or they may have any other cross-sectional configuration, including a varying cross-sectional configuration, that may be appropriate to achieve the desired fluid flow characteristics. Rate control plate 246 can be constructed from the same materials and in the same manner as was the earlier described rate control plate 146.

The important priming means of this latest form of the invention, which comprises prime channel 243, functions to purge gases from the fluid passageways of the device and to prime the various fluidic elements of the device before the medicinal fluid contained within the fluid reservoirs is delivered to the administration set. This feature of the apparatus ensures that only the desired fluid is delivered at the outlet passageway 130 of the device during normal operation and that the device is in a state in which it will deliver fluid to the outlet passageway in as short a time as possible. In this regard it is to be noted that each of the fluidic micro channels is provided with an inlet that is in communication with prime channel 243 so that as the prime channel is filled, each of the fluidic micro channels will also fill via the filter "F". Prime channel 243 is also in communication with a prime channel outlet port 243a, which, in turn, communicates with an inlet port 267 formed in upper portion 244a of the rate control housing. Any gases trapped within the fluidic micro channels can be vented to atmosphere via vent means, shown in FIG. 26 as a vent "V-1".

As the various fluid flow passageways of the device fill with fluid during the priming step, gases contained within the various communicating passageways will be vented to atmosphere via the earlier identified vent means "V" of the invention which is formed in the outer housing 34 (FIG. 4). The vent means in this latter form of the invention preferably comprises a porous hydrophobic material such as a porous plastic. The pores of the vent should have a diameter of no more that 2 μm. It is well known that aqueous fluid will not move through capillaries (holes) on the order of 2 μm in diameter in hydrophobic material under the pressures contemplated for use in this device of this latest form of the invention (pressures of approximately 1 ATM or less). However, there are also commercial hydrophobic porous vents made from sintered porous polyethylene available from companies such as the Porvair Filtration Group. Many of these vents have pore sizes of 10-100 microns and are commonly used as medical fluid vent plugs. Vent "V" could also be provided in the form of a cylinder with a diameter of approximately 1 mm and a length of approximately 1 mm.

In operating the apparatus of this latest form of the invention, once the apparatus reservoirs have been filled with the appropriate fluids using the syringe fill assemblies 84 in the manner illustrated in FIGS. 22 and 23, either of the fluids contained within the reservoirs, or a mixture of the fluids can be delivered to the patient at a precise rate through manipulation of the selector knobs 170 and 170a, which are of identical construction and operation to those previously described herein. As before, the rate of fluid delivery to the patient is selected by controllably rotating selector knobs 170 and 170a within their respective vertical bores 172 and 172a (see FIG. 4). Such rotation will permit the passageways 182, which are formed within each of the selector knobs (see also FIG. 12), to be moved into alignment with a selected one of the circumferentially spaced outlet ports 255a, 257a, 259a, 261a, 263a and 265a of the cover, or top portion 244 of the rate control assembly with which the knob is associated.

Referring once again to FIGS. 4, 24 and 26, and, by way of example, during the delivery of fluid contained within first reservoir 44 of the apparatus to the patient via the administration set 124, as the pusher assembly 68 is urged forwardly by the stored energy means, or spring 62, the medicinal fluid contained within reservoir 44 will flow through reservoir outlet port 48, through a passageway 186 formed in the device housing and into inlet 250i of upper portion 244a of rate control assembly 242 (see FIG. 26). As the fluid flows into inlet 250i, which incorporates a filter "F", the priming channels 248 as well as each of the micro channels of the rate control plate 246 will fill with the medicinal fluid. When the selector knob 170 is in the priming position shown in FIG. 26, the fluid will flow from a priming channel 248 into passageway 243, toward the outlet 267 and into the various passageways formed in the reservoir selector member 190. From selector member 190 the priming fluid will flow into vent passageway 120a and into the fluid delivery passageway 130 (FIG. 4) in a manner to prime these passageways with fluid and to purge any gases contained therein or to atmosphere via the vent means.

When the selector knob 170 is rotated to a position wherein passageway 182 of the selector knob is aligned with the outlet of one of the micro channels of the rate control plate 246, such as the outlet of passageway 255, fluid will flow from micro channel 255 into passageway 182, then into passageway 187 which is in communication therewith and then into an annular passageway 189 which is in communication with passageway 187 (FIGS. 4, 24, 25 and 26). Delivery of fluid to the patient from second reservoir 50 of the apparatus is accomplished in a similar manner through rotation of selector member, or knob 170a within bore 172a to align passageway 186 of this selector knob with one of the micro channels of the rate control plate with which knob 170a is associated. From passageways 189 of the selector knob, the fluid will flow toward the third, or reservoir selector member 190 via a passageway 192 formed in the apparatus housing. As in the earlier described embodiment of the invention, reservoir selector member 190, which is identical in construction and operation to that previously described, functions to control fluid flow from either or both of the rate control assemblies toward the patient via administration set 124. From passageways 192, the fluid will flow into a connector passageway 194, which is formed within reservoir selector member 190 and which functions to permit fluid flow from either of the annular passageways 189 formed in the selector knobs or from a cross-connect passageway 196 formed in the device housing (FIG. 24), which interconnects the annular flow passageways 189 of selector knobs 170 and 170a (see also FIGS. 13, 24 and 25). As previously described herein, this permits fluid flow toward the patient from a selected one of the fluid reservoirs 44 and 50, or alternatively simultaneously from both of the reservoirs via reservoir selector member 190.

Also forming a part of the flow control means of the invention is selector knob-locking means for preventing rotation of selector knobs 170 and 170a. This selector knob-locking means is identical in construction and operation to that previously described in connection with the first embodiment of the invention.

It is important to note that priming of the various fluid passageways of the device ensures that only the desired fluid is delivered at the output of the device during normal operation and that the device is in a state in which it will deliver fluid at the exit of the output capillary in a reasonably short time. The value of the priming means of this latest form of the invention is evident from a study of FIG. 27 of the drawings which comprises a table of the fluidic properties of one form of the flow rate control member, the flow rate selector means and the administration line for the distal rate control device of this latest form of the invention. For purposes of illustration in FIG. 27, the flow rates are shown to be from 0.1 to 5.0 ml/hr and the rate defining channels are assumed to be 4000 $\mu m^2$ to 40,000 $\mu m^2$. Similarly, the priming channel is assumed to be 1000 $\mu m \times 100$ $\mu m$ wide×deep, the channel in the rate control selector means is assumed to be 1 mm in diameter and 3 cm long and the administration line is assumed to be 1 meter long and 40 thousandths of an inch (approx. 1 mm) in diameter I.D. The priming channels on the chip, the channel in the flow rate selector means and the administration line are treated as one item for the purpose of priming time and flow rate. It is to be understood that the surface characteristics of the various fluidic micro channels may be tailored to impart desired fluid flow characteristics.

From a study of FIG. 27 it can be seen that if one of the flow rate defining fluidic micro channels were used to prime the administration line, then there would be an unreasonably long time between the time that the device is initially "turned on" and the time that fluid is delivered from the administration line. This is because the volume of the administration line is 0.785 ml. For example, suppose the flow rate is 0.5 ml/hr then it would be 94 minutes (i.e., 0.785 ml/0.5 ml/hr=1.57 hours) before fluid emerges from the administration line and the device is ready to use. This length of time to wait before the device is ready to use is undesirable in most applications of the device. It is evident that a priming means envisioned by this latest form of the device of the invention is an advantageous feature which enables the device be ready to administer fluid in a matter of a minute or less.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. A dispensing apparatus for dispensing fluids to a patient at a controlled rate comprising a housing having:
   (a) a first fluid reservoir for containing fluid to be dispensed to the patient, said housing being provided with a first inlet for permitting fluid flow into said first fluid reservoir and a first outlet for permitting fluid flow from said first fluid reservoir;
   (b) a first pusher assembly disposed within said housing for movement between a first position and a second position to cause said fluid contained within said first fluid reservoir to flow toward said first outlet;
   (c) a first spring disposed within said housing for acting upon said first pusher assembly to cause said first pusher assembly to move toward said second position;
   (d) a first fill assembly carried by said housing for filling said first fluid reservoir with the fluid to be dispensed;
   (e) a first rate control assembly carried by said housing for controlling fluid flow from said first fluid reservoir to the patient;
   (f) a second fluid reservoir for containing fluid to be dispensed to the patient, said housing being provided with a second inlet for permitting fluid flow into said second fluid reservoir and a second outlet for permitting fluid flow from said second fluid reservoir;
   (g) a second pusher assembly disposed within said housing for movement between a first position and a second position to cause said fluid contained within said second fluid reservoir to flow toward said second outlet;

(h) a second spring disposed within said housing for acting upon said second pusher assembly to cause said second pusher assembly to move toward said second position;

(i) a second fill assembly carried by said housing for filling said second fluid reservoir with the fluid to be dispensed;

(j) a second rate control assembly carried by said housing for controlling fluid flow from said second fluid reservoir to the patient;

(k) an administration set connected to said housing and in communication with said first and second rate control assemblies for dispensing fluid to the patient; and (l) a selector member carried by said housing for controlling fluid flow from said first and second rate control assemblies toward said administration set.

2. The apparatus as defined in claim 1 in which said housing further includes a first connector portion and in which said first fill assembly comprises a first fill syringe assembly interconnectable with said first connector portion, said first fill syringe assembly comprising:
(a) a hollow housing having a chamber; and
(b) a fill vial telescopically receivable with and said chamber of said hollow housing, said fill vial having a fluid reservoir and a plunger disposed within said fluid reservoir for movement between first and second positions.

3. The apparatus as defined in claim 1 in which said housing further includes a second connector portion and in which said second fill assembly comprises a second fill syringe assembly interconnectable with said second connector portion, said second fill syringe assembly comprising:
(a) a hollow housing having a chamber; and
(b) a fill vial telescopically receivable within said chamber, said fill vial having a fluid reservoir and a plunger disposed within said fluid reservoir for movement between first and second positions.

4. The apparatus as defined in claim 1 in which said first rate control assembly further includes a first flow rate control member mounted within said housing, said first flow rate control member having a plurality of elongated fluidic flow control channels in communication with said first fluid reservoir.

5. The apparatus as defined in claim 4 in which said plurality of elongated fluidic flow control channels of said first flow rate control member have a depth of approximately 1-1000 µm.

6. The apparatus as defined in claim 1 in which said second rate control assembly further includes a second flow rate control member mounted within said housing, said second flow rate control member having a plurality of elongated fluidic flow control channels in communication with said second fluid reservoir.

7. The apparatus as defined in claim 1 in which each of said first and second rate control assemblies further comprise a priming channel for priming said fluid passageways formed therein.

8. The apparatus as defined in claim 1 further including a disabling member carried by said housing for irrevocably disabling the device and rendering it inert.

9. The apparatus as defined in claim 8 in which said disabling member comprises a disabling shaft that is telescopically movable within a fluid outlet passageway formed within said housing.

10. A dispensing apparatus for dispensing fluids to a patient comprising:
(a) a housing having a fluid reservoir for containing fluid to be dispensed to the patient, said housing being provided with an inlet for permitting fluid flow into said fluid reservoir and an outlet for permitting fluid flow from said fluid reservoir;
(b) a pusher assembly disposed within said housing for movement between a first position and a second position to cause said fluid contained within said fluid reservoir to flow toward said outlet;
(c) a spring disposed within said outer housing for acting upon said pusher assembly to cause said pusher assembly to move toward said second position;
(d) a fill assembly carried by said housing for filling said reservoir with the fluid to be dispensed;
(e) a rate control assembly carried by said housing for controlling fluid flow from said reservoir to the patient, said rate control assembly comprising:
(i) a flow rate control member mounted within said housing, said flow control member having a plurality of elongated fluidic flow control channels in communication with said fluid reservoir;
ii) a priming channel for priming said plurality of elongated fluidic micro channels with fluid from said reservoir; and
(f) an administration set connected to said housing and in communication with said plurality of elongated fluidic flow control channels.

11. The apparatus as defined in claim 10 in which said housing includes a vial receiving chamber and in which said fill assembly comprises a fill vial receivable within said vial receiving chamber.

12. The apparatus as defined in claim 10 in which said plurality of elongated fluidic flow control channels of said flow rate control member have a depth of approximately 10-100 µm.

13. The apparatus as defined in claim 10 in which said housing further includes a connector portion and in which said fill assembly comprises a pierceable septum mounted within said housing and a fill syringe assembly interconnectable with said connector portion, said fill syringe assembly comprising:
(a) a hollow housing having a chamber; and
(b) a fill vial telescopically receivable within said chamber of said hollow housing, said fill vial having a fluid reservoir and a plunger disposed within said fluid reservoir for movement between first and second positions.

14. The apparatus as defined in claim 10 further including a disabling member carried by said housing for irrevocably disabling the device and rendering it inert.

15. The apparatus as defined in claim 14 in which said disabling member comprises a disabling shaft that is telescopically movable within a passageway formed within said housing.

16. The apparatus as defined in claim 10, further comprising a vent carried by said housing and in communication with said flow rate control member for venting to atmosphere gases contained within said plurality of elongated fluidic micro channels.

17. The apparatus as defined in claim 10 further comprising reservoir volume indicator for indication of the volume of fluid within said fluid reservoir.

18. The apparatus as defined in claim 10 in which said fluidic micro channels have surfaces, said surfaces being modified to provide unique surface characteristics.

19. The apparatus as defined in claim 10 in which said fluid reservoir comprises a closed in bellows structure.

20. The apparatus as defined in claim 19 in which said bellows structure has internal surfaces said surfaces being modified to provide drug and environmental compatibility.

* * * * *